United States Patent [19]

Lake

[11] Patent Number: 4,573,461

[45] Date of Patent: Mar. 4, 1986

[54] NASAL SEALER AND FILTER

[76] Inventor: Norman M. Lake, 1705 Newport Dr., Lancaster, Pa. 17602

[21] Appl. No.: 542,715

[22] Filed: Oct. 17, 1983

Related U.S. Application Data

[63] Continuation-in-part of Ser. No. 288,056, Jul. 29, 1981, abandoned.

[51] Int. Cl.[4] .......... A61M 16/00

[52] U.S. Cl. .......... 128/201.18; 128/206.11; 128/204.17

[58] Field of Search .......... 128/206.11, 201.18, 128/204.17

[56] References Cited

U.S. PATENT DOCUMENTS 3,145,711 8/1964 Bober .......... 128/206.11

FOREIGN PATENT DOCUMENTS 505613 8/1930 Fed. Rep. of Germany .......... 128/201.18

OTHER PUBLICATIONS

Couch, 5/24/74, Letter from Dr. Robert B. Couch, M.D. to Norman N. Lake about research involving inventive concept.

*Primary Examiner*—Henry J. Recla

[57] ABSTRACT

Protection for the nasal passages comprising an oblong ellipsoid-shaped solid of soft pliable impervious material called a sealer or arrester for inserting and closing off the nasal cavities.

When the same solid is made of soft, pliable and porous material, its function will be that of a nasal filter when inserted in the nasal cavities.

2 Claims, 3 Drawing Figures

FIG.2
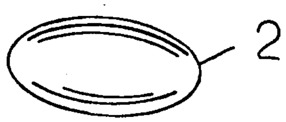
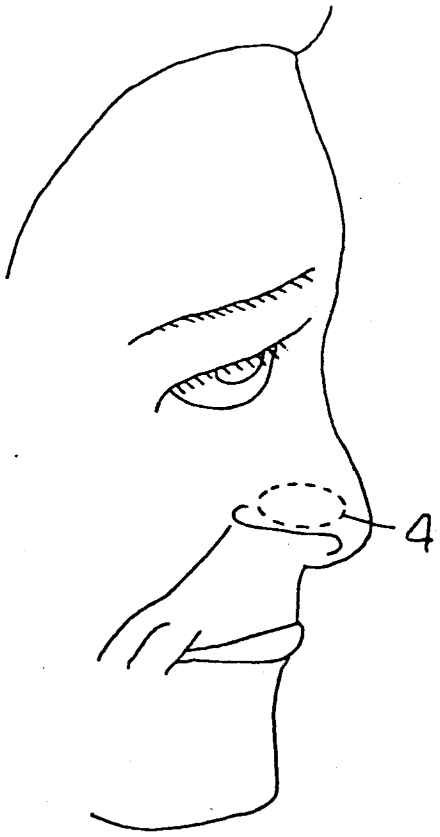
FIG.1
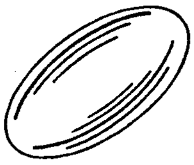
FIG.3

NASAL SEALER AND FILTER

This application is a continuation-in-part of Application Ser. No. 288,056, filed July 29, 1981 and now abandoned, entitled "Nasal Sealer and Filter".

This invention is an improvement over that of my Application Ser. No. 610,655, filed Sept. 5, 1975, entitled "Nasal Protective Splint" and issued as U.S. Pat. No. 4,033,342 on July 5, 1977.

Additionally, while this device will perform the same functions as that set forth in my Application Ser. No. 183,214 filed Sept. 2, 1980and now abandoned, it provides the individual the important alternative of an invisible device when worn in public, compared to one worn on the outside of the nose and considered unsightly by some individuals to wear in public.

SUMMARY OF THE INVENTION

The device of this invention is a nasal sealer having an oblong ellipsoid-shaped solid of soft pliable air impervious material used to insert and seal off each of the nasal cavities when a person is threatened by harmful material breathed into the nose.

The sealing off of the nose at such a time prevents irritating agents and cool air from entering the nasal passages and during the lapse of 30 minutes or more, the nasal temperature will rise sufficiently to create a condition in the nose having certain characteristics similiar to inflammation, the natural defensive reaction to irritation, but without the pain and suffering of inflamed and swollen membranes. That is, the phrase "having certain characteristics similiar to inflammation" means creating only the raised temperature and nasal obstruction normally associated with inflammation and not the other three characteristics of inflammation; namely, pain, redness and swelling.

Immediately following this period of time (30 minutes), the solid seals are removed from inside the nose and replaced by the same type of seal except it is porous to allow for breathing through the nose and functioning as a filter.

U.S. Pat. No. 2,274,997, issued Mar. 3, 1942 to G. C. Thurman, relates to plugs inserted in the nose and used by swimmers to prevent water from entering the nasal passages. When the plugs of said patent are being worn, the external extensions of the stems 4, the lateral projecting arms 5 and the metallic connector with its projections 8,9 and 10 are all superflous with respect to my invention. These would be unnecessary extensions adding weight and increased cost of manufacture. The metallic connector 7 is not adjustable which could result in the force by the arms 5 on the external end of the nasal septum 6 being either too much for comfort or insufficient to maintain the plugs in the proper position inside the nose. Additionally, the outer extensions being located under the nose tend to create unsightliness and a health hazard if worn for the use of my invention in that they could become contaminated with infectious secretions from the nose and induce the spread of infection to nearby persons. Moreover, the patent does not teach the use of my invention to seal off the nose for the principal purpose of creating a condition therein "having certain characteristics similiar to inflammation", inflammation being the natural defensive reaction to irritation.

BRIEF DESCRIPTION OF DRAWINGS

FIG. 1 illustrates the nasal seal and filter in use.

FIG. 2 is a side elevation of seal and filter.

FIG. 3 is a perspective view of seal and filter.

DESCRIPTION OF THE PREFERRED EMBODIMENTS

This invention relates to an improvement in nasal protectors and has for its principal object protection of the mucous membranes of the nasal passages. To this end inhalation of airborne irritants and cool air entering the nose is prevented.

Toward this objective, the nose of the human is closed off completely by inserting a nasal seal comprising an oblong ellipsoid-shaped solid 2 of soft pliable air impervious material such as closed cell thermoplastic material or densified cotton fibers into each nasal cavity 4 for a period of 30 or more minutes to create a nasal obstruction and a raised temperature environment within the nasal passages, while keeping allergens, infectious agents and cool air out of the nose. During this time, a condition in the nose has been established "having certain characteristics similiar to inflammation", inflammation being the natural defensive reaction to irritation.

It is now well known fact that the average normal temperature in the nose is 91.4° F. In the mouth and core body, it is 98.6° F. Clinical research has proven that, when the nose is closed off from the atmosphere, the temperature therein rises in a matter of minutes to that approaching 98.6° F. Why is this important? It is important for the following reasons.

When a person comes down with an acute head cold, it usually takes from 36 to 48 hours to reach its peak of development, during which time the victim is truly miserable. At the end of this time, the peak of nasal obstruction has been reached, i.e., the nasal mucosa has become inflamed and its swelling closes off the nasal passages. This is the critical and turning point in cold infection when all the symptoms begin to subside, but it takes five or more days for them to disappear.

When the nasal mucosa became inflamed and swollen, the heat generated began to inhibit the growth of the common cold viruses and the condition of inflammation triggers the alarm of the victim's immune system ushering in the army of white blood cells that include leukocytes, especially the granular ones that are phagocytic, i.e., have the power to ingest bacteria, virus, pollen, dust and all such irritating agents.

Thus the heat from the inflamed membranes inhibits the growth of viruses and the swelling together with increased heat constitute an injury that incites the white blood cells into action and overcomes allergens responsible for allergies. This method which the body finally develops to overcome the common cold and nasal allergies is nature's "last resort" and prevents those nasal disorders from being fatal.

In fact, this improvement of prolonging the time of closing off the nasal passages for 30 minutes or more which creates heat inside the nose as compared to that of only two or three minutes called for in my U.S. Pat. No. 4,033,342 for inhibiting sneezing, is precisely the difference between failure and success in simulating part of the natural inflammatory process and arresting nasal disorders.

So when the nose is threatened by harmful material breathed into the nose as evidenced by sneezing, dripping nose or a slight scratchy feeling in the throat, this nasal sealer should promptly be inserted in and used to seal off each of the nasal cavities and remain there for 30 minutes or more. Then, immediately following this period, one replaces the solid seal in each nasal cavity with the nasal filter comprising an ellipsoid-shaped device of soft pliable porous material such as nylon or cotton fiber of precisely the same size as the nasal sealer to trap and minimize harmful material entering the nose. This filter can be worn as long as desired with a minimum of discomfort. Should the nose again be threatened by foreign material, one replaces the porous filter with a sealer in each nasal cavity for the time as set forth above.

This invention resides not merely in using a nasal plug, but devising a nasal protective seal for a new and inventive use. The prime object of the invention is to fulfill a health need long desired but never attained which fact is manifested by its absence of availability for public benefit. My invention is novel since it is out of the ordinary and unobvious because it is insufficiently evident to arrest attention.

In the tests to determine rise in temperature in the nasal passages when the nose is sealed shut, the following temperatures were recorded:

| Time Nose Closed Off (min.) | Temperature in Nasal Passages |
|---|---|
| | Test 1 |
| 0 | 33.5° C. (92.3° F.) |
| 5 | 35.8° C. (96.4° F.) |
| 10 | 36.4° C. (97.5° F.) |
| 15 | 36.5° C. (97.7° F.) |
| 20 | 36.5° C. (97.7° F.) |
| 25 | 36.7° C. (98.1° F.) |
| 30 | 36.7° C. (98.1° F.) |
| | Test 2 |
| 0 | 33.0° C. (91.4° F.) |
| 5 | 35.8° C. (96.4° F.) |
| 10 | 36.4° C. (97.5° F.) |
| 15 | 36.6° C. (97.8° F.) |
| 20 | 36.6° C. (97.8° F.) |

During both tests, the temperature in the mouth was 97.4° F. The average normal temperature in the nose is 33° C. (91.4° F.). The higher temperatures in the nose are in the range of inflamed nasal mucous membranes, a vital defensive reaction of inflammation.

Having thus described my invention, what I claim as new and desire to secure by Letters Patent is:

1. A new process of employing a particular seal and filter for helping the human nose maintain its mucous membranes in good condition, the seal comprising an oblong ellipsoid shaped solid of soft pliable impervious material, the filter differing therefrom only by being porous, the steps of:

(a) inserting into each nasal cavity a solid seal to close off the nasal passages promptly when the nose is threatened by harmful material breathed therein as evidenced by sneezing, dripping nose and often a slight scratchy feeling in the throat, this being done for a period of 30 minutes or more for the purpose of invisibility, and preventing cool air, infectious and allergenic agents from entering the nose, while simultaneously increasing the temperature within the nose, thereby creating an environment therein that inhibits growth of the common cold virus and establishing in the nose a condition "having certain characteristics similiar to inflammation", but without the pain and suffering of inflamed and swollen membranes;

(b) then immediately following the 30 minutes or more time period, the solid seal in each nasal cavity is replaced by a filter of soft pliable, but porous, material of precisely the same size and shape as the nasal seal for trapping and minimizing harmful material entering the nose, this porous filter can be worn as long as desired with a minimum of discomfort; and, (c) when the nose again is threatened by harmful material, the porous filter can be replaced with the solid seal in each nasal cavity for the time period as set forth above.

2. The process of claim 1 wherein:

(a) the increased temperature in the nose is raised to about 98.6° F. which is the temperature occurring during natural inflammation.

* * * * *